(12) United States Patent
Nishimura et al.

(10) Patent No.: US 8,535,942 B2
(45) Date of Patent: Sep. 17, 2013

(54) GLYPICAN-3 (GPC3)-DERIVED TUMOR REJECTION ANTIGENIC PEPTIDES USEFUL FOR HLA-A2-POSITIVE PATIENTS AND PHARMACEUTICAL COMPRISING THE SAME

(75) Inventors: Yasuharu Nishimura, Kumamoto (JP); Tetsuya Nakatsura, Chiba (JP); Hiroyuki Komori, Kumamoto (JP)

(73) Assignee: Oncotherapy Science, Inc., Kanagawa (JP)

( * ) Notice: Subject to any disclaimer, the term of this patent is extended or adjusted under 35 U.S.C. 154(b) by 0 days.

(21) Appl. No.: 13/242,019

(22) Filed: Sep. 23, 2011

(65) Prior Publication Data
US 2012/0040452 A1    Feb. 16, 2012

Related U.S. Application Data

(62) Division of application No. 12/063,165, filed as application No. PCT/JP2006/315631 on Aug. 8, 2006, now Pat. No. 8,053,556.

(30) Foreign Application Priority Data

Aug. 9, 2005  (JP) ................................ 2005-230702

(51) Int. Cl.
*C12N 5/00* (2006.01)
*C12N 5/02* (2006.01)
*C12N 5/08* (2006.01)
*A61K 39/38* (2006.01)
*A61K 39/385* (2006.01)

(52) U.S. Cl.
USPC ........ 435/372; 435/325; 435/366; 424/184.1; 424/185.1; 424/193.1

(58) Field of Classification Search
None
See application file for complete search history.

(56) References Cited

U.S. PATENT DOCUMENTS

| | | | |
|---|---|---|---|
| 7,303,914 B2 | 12/2007 | Wang et al. | |
| 8,017,345 B2 | 9/2011 | Nishimura et al. | |
| 8,053,556 B2 | 11/2011 | Nishimura et al. | |
| 8,053,557 B2 | 11/2011 | Nishimura et al. | |
| 2004/0253606 A1 | 12/2004 | Aziz et al. | |
| 2008/0044818 A1 | 2/2008 | Nishimura et al. | |

FOREIGN PATENT DOCUMENTS

| | | | |
|---|---|---|---|
| CA | 2 497 744 | | 9/2003 |
| CN | 1379041 A | | 11/2002 |
| WO | WO 99-37764 | * | 7/1999 |
| WO | 01/47944 | | 7/2001 |
| WO | 2004/018667 A1 | | 3/2004 |
| WO | 2004/022739 A1 | | 3/2004 |
| WO | 2004/038420 A1 | | 5/2004 |
| WO | 2005/039380 A2 | | 5/2005 |

OTHER PUBLICATIONS

Sung et al. Glypican-3 is overexpressed in human hepatocellular carcinoma. Cancer Sci. 94(3): 259-262, Mar. 2003.*
Parker et al., "Scheme for Ranking Potential HLA-A2 Binding Peptides Based on Independent Binding of Individual Peptide Side-Chains," *J. Immunol.* 152(1):163-175 (1994).
Nakatsura et al., "Glypican-3, overexpressed specifically in human hepatocellular carcinoma, is a novel tumor marker" *Biochem. Biophys. Res. Commun.* 306:16-25 (2003).
Nakatsura et al., "Identification of Glypican-3 as a Novel Tumor Marker for Melanoma" *Clin. Cancer Res.* 10:6612-6621 (2004).
Köhler et al., "Continuous cultures of fused cells secreting antibody of predefined specificity" *Nature* 256:495-497 (1975).
Takahashi et al., "Induction of CD8+ cytotoxic T cells by immunization with purified HIV-1 envelope protein in ISCOMs" *Nature* 344:873-875 (1990).
Mouritsen et al., "pH Dependence of the Interaction Between Immunogenic Peptides and MHC Class II Molecules" *J. Immunol.* 148(5): 1438-1444 (1992).
Nakatsura et al., "Cellular and humoral immune responses to a human pancreatic cancer antigen, coactosin-like protein, originally defined by the SEREX method" *Eur. J. Immunol.* 32:826-836 (2002).
Monji et al., "Identification of Novel Human Cancer/Testis Antigen, KM-HN-1, Recognized by Cellular and Humoral Immune Responses" *Clin. Cancer Res.* 10:6047-6057 (2004).
H. Komori et al., "Identification of HLA-A2- or HLA-A24-Restricted CTL Epitopes Possibly Useful for Glypican-3-Specific Immunotherapy of Hepatocellular Carcinoma," *Clin. Cancer Research*, vol. 12, No. 9, pp. 2689-2697 (2006).
Y. Motomura et al., "HLA-A2 and -A24-Restricted Glypican-3-Derived Peptide Vaccine Induces Specific CTLs: Preclinical Study Using Mice," *International Journal of Oncology*, vol. 32, pp. 985-990 (2008).
Australian Office Action that issued with respect to patent family member Australian Patent Application No. 2006277295, dated Jan. 31, 2011.
Nukaya et al., "Identification of HLA-A24 Epitope Peptides of Carcinoembryonic Antigen Which Induce Tumor-Reactive Cytotoxic T Lymphocyte" *Int. J. Cancer* 80(1):92-97, 1999.
Pilia et al., "Mutations in GPC3, a Glypican Gene, Cause the Simpson-Golabi-Behmel Overgrowth Syndrome" *Nature Genetics* 12(3):241-47, 1996.

(Continued)

*Primary Examiner* — Alana Harris Dent

(74) *Attorney, Agent, or Firm* — Greenblum & Bernstein, P.L.C.

(57) ABSTRACT

It is an object of the present invention to identify a glypican-3-derived peptide which can bind to HLA-A2 and activate human killer T cells, so as to provide a means for carrying out an immunotherapy which is able to target approximately 40% of Japanese patients suffering from several types of cancers, which express GPC3 at a high level. The present invention provides a peptide of any of the following (A) or (B):

(A) a peptide, which has the amino acid sequence as shown in any one of SEQ ID NOS: 1 to 3; or
(B) a peptide, which has an amino acid sequence comprising a substitution or addition of one or two amino acids with respect to the amino acid sequence as shown in any one of SEQ ID NOS: 1 to 3, and which has ability to induce killer T cells.

3 Claims, 2 Drawing Sheets

(56) References Cited

OTHER PUBLICATIONS

Zhu et al., "Enhanced Glypican-3 Expression Differentiates the Majority of Hepatocellular Carcinomas from Benign Hepatic Disorders" *Gut* 48(4):558-64, 2001.

Nakatsura et al., Proceedings Sixty-First Annual Meeting of the Japanese Cancer Association, vol. 93 Supplement, p. 378, 1338 "Glypican-3, overexpressed specifically in human hepatocellular carcinoma, may prove to be novel tumor marker and potential candidate for immunotherapy" (2002), along with an English language translation.

Greenspan et al. Nature Biotechnology 17:936 and 937, 1999.

Blythe et al. Protein Science. 14: 246-248, 2005.

Chamberlain et al. Expert Opinion on Phamacotherapy 1(4):603-614, 2000.

Bodey et al. Anticancer Research 20: 2665-2676, 2000.

Gura et al. Science 278: 1041 and 1042, Nov. 7, 1997.

U.S. Appl. No. 13/243,259 to Yasuharu Nishimura et al., filed Sep. 23, 2011.

Rock et al., "Analysis of the Association of Peptides of Optimal Length to Class I Molecules on the Surface of Cells" *Proc. Natl. Acad. Sci. USA*, vol. 89, pp. 8918-8922, 1992.

Bristol et al., "Development of a Murine Mutant Ras CD8[+] CTL Peptide Epitope Variant That Possesses Enhanced MHC Class I Binding and Immunogenic Properties" *J. Immunol.*, vol. 160, No. 5, pp. 2433-2441, 1998.

Maecker et al., "Cytotoxic T Cell Responses to DNA Vaccination: Dependence on Antigen Presentation via Class II MHC" *J. Immunol.*, vol. 161, No. 12, pp. 6532-6536, 1998.

Japanese Office Action issued with respect to patent family member Japanese Patent App. No. 2007-529588, mailed Feb. 28, 2012, In Japanese. No English translation.

Chinese Office Action issued with respect to patent family member Chinese Patent App. No. 200680037419.8, dated Jul. 3, 2012, No English translation.

Japanese Office Action issued with respect to Japanese Patent App. No. 2007-529588, mailed Oct. 16, 2012, along with an English-language excerpt.

Canadian Office Action issued with respect to patent family member Canadian Patent App. No. 2,619,443, dated Jul. 19, 2012.

Canadian Office Action issued with respect to patent family member Canadian Patent App. No. 2,619,443, dated Jun. 10, 2013.

\* cited by examiner

Fig..2
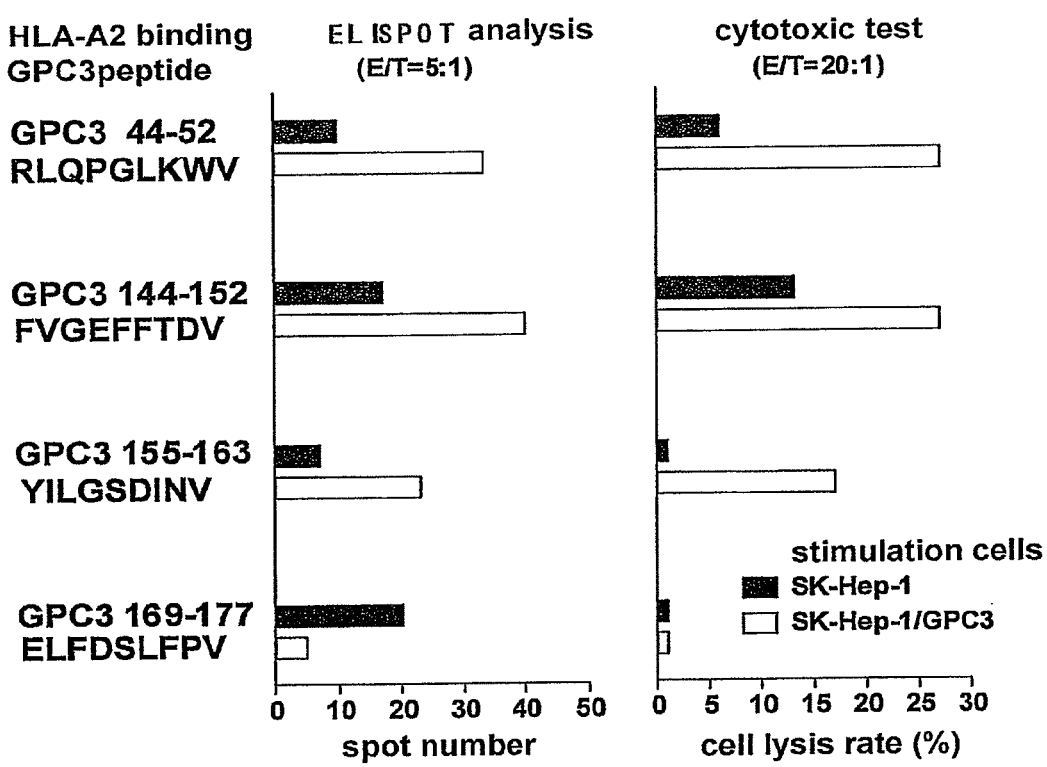

```
                         SEQUENCE LISTING

<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Leu Gln Pro Gly Leu Lys Trp Val
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Val Gly Glu Phe Phe Thr Asp Val
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Ile Leu Gly Ser Asp Ile Asn Val
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Leu Phe Asp Ser Leu Phe Pro Val
1               5
```

GLYPICAN-3 (GPC3)-DERIVED TUMOR REJECTION ANTIGENIC PEPTIDES USEFUL FOR HLA-A2-POSITIVE PATIENTS AND PHARMACEUTICAL COMPRISING THE SAME

CROSS-REFERENCE TO RELATED APPLICATIONS

This application is a Divisional of U.S. patent application Ser. No. 12/063,165, which is the National Stage of International Application No. PCT/JP2006/315631, filed Aug. 8, 2006, the disclosure of which is incorporated herein by reference. This application also claims priority to Japanese Patent Application No. JP 2005-230702, filed Aug. 9, 2005.

TECHNICAL FIELD

The present invention relates to novel peptides that are effective as a vaccine for cancers highly expressing glypican-3 (GPC3), such as hepatocellular carcinoma or malignant melanoma (melanoma), and a pharmaceutical comprising the aforementioned peptides used for treating and preventing tumors.

BACKGROUND ART

Primary hepatocellular carcinoma is a malignant disease that occurs at a high frequency in various countries over the world. As a result of large outbreaks of hepatitis B and C over the world, the incidence of hepatocellular carcinoma has been rapidly increasing in Asian and European countries. Taking into consideration the long incubation period from infection with hepatitis virus to the onset of the disease, it is anticipated that such tendency will continue over the coming fifty years. Hepatocellular carcinoma whose condition has become worse has a poor prognosis. Thus, it is desired to rapidly develop a new treatment strategy.

On the other hand, with the development of molecular biology and tumor immunology in recent years, it has been revealed that cytotoxic (killer) T cells and helper T cells recognize peptides formed by decomposition of proteins highly expressed specifically in cancer cells, which are presented on the surfaces of the cancer cells or antigen-presenting cells via HLA molecules, and that they exhibit an immune reaction for destroying such cancer cells. Moreover, a large number of tumor antigenic proteins and peptides, which stimulate such an immune reaction to attack cancers, have been identified, and clinical application of an antigen-specific tumor immunotherapy has been advanced.

HLA class I molecules are expressed on the surfaces of all nuclear cells in a body. Peptides derived from decomposed cytoplasmic and nuclear proteins are bound to HLA class I molecules, and they are expressed on the surfaces of such cells. On the surfaces of normal cells, peptides derived from normal autologous proteins bind to HLA class I molecules, and T cells of the immune system neither recognize nor respond to such peptides bound to HLA class I molecules. On the other hand, in a process in which normal cells are converted to a cancer, such cancer cells may express large amounts of proteins, which are hardly expressed or are only expressed in small amounts in normal cells. If a peptide generated by decomposition in the cytoplasm of such a protein that is highly and specifically expressed in a cancer cell binds to an HLA class I molecule and is expressed on the surface of such a cancer cell, a killer T cell recognizes the peptide and destroys only the cancer cell. In addition, by administering such a cancer-specific antigen or peptide to an individual body, it is possible to destroy cancer cells and suppress the growth of a cancer, without impairing normal cells. This is referred to as cancer immunotherapy using a cancer-specific antigen. Moreover, an HLA class II molecule is mainly expressed on the surface of an antigen-presenting cell. Such an HLA class II molecule binds to a peptide derived from a cancer-specific antigen generated by incorporating the cancer-specific antigen from outside the cell and decomposing it in the cell, and it is expressed on the surface of the cell. A helper T cell, which has recognized the peptide bound by HLA class II molecule, is activated to generate various cytokines that activate other immunocompetent cells, so as to induce or reinforce an immune reaction against a tumor.

Thus, if an immunotherapy targeting an antigen that is highly and specifically expressed in such a cancer can be developed, it can become a treatment method for effectively eliminating the cancer alone, without impairing normal autologous organs. Moreover, it is anticipated that such an immunotherapy can become a treatment method applicable to patients suffering from a terminal-stage cancer, for whom no other treatments can be implemented. Furthermore, if a cancer-specific antigen and peptide are administered in the form of a vaccine to a human having a high risk of developing such a cancer, there is a possibility that the onset of the cancer can be prevented.

It has been reported that, in normal tissues, an α-fetoprotein (AFP) is expressed only in the prenatal period, and that it is what is called a carcinoembryonic protein whose expression is activated again in many hepatocellular carcinomas. In addition, several types of mouse and human T cells recognize a peptide epitope derived from APP presented by an MHC class I molecule. During the developmental stage, a fetus is exposed to AFP existing at a high level in plasma. However, mature T cells do not acquire complete immunological tolerance to AFP, and AFP-specific T cells are detected in peripheral blood. That is to say, such a carcinoembryonic protein can be a target of immunotherapy.

There are various methods for treating hepatocellular carcinoma. However, the prognosis of such hepatocellular carcinoma is worse than those of other types of cancers, and thus this cancer is considered to be an intractable cancer. This may be because hepatocellular carcinoma develops on the basis of liver cirrhosis and thus patients with hepatocellular carcinoma have poor hepatic functions. This may also be because although a mass of cancer has been treated, another cancer develops from another site. Accordingly, it has been necessary to rapidly develop a novel treatment strategy. If an immunotherapy targeting an antigen that is highly and specifically expressed in hepatocellular carcinoma can be developed, there is a possibility that such an immunotherapy will become a therapeutic method for effectively eliminating cancer alone without impairing normal autologous organs. Moreover, it is anticipated that the aforementioned immunotherapy can be a therapeutic method, which is available for patients who are in terminal stage of cancer, and further, for patients whose hepatic functions are too poor to allow other treatments to be carried out. At present, it is said that, in Japan, more than 2,000,000 people are infected with hepatitis C virus, and that such people are, potential hepatocellular carcinoma patients. There is a possibility that the aforementioned immunotherapy will be also applied to prevent such infected patients from actually being suffering from hepatocellular carcinoma.

Melanoma is one type of skin cancer, which is often called malignant melanoma. There are many types of skin cancers. Among such skin cancers, melanoma is classified as having the highest grade of malignancy, and thus it is greatly feared.

Among cells that constitute skin, several cells generate melanin pigment. Such cells are called melanocytes. When such melanocytes become cancerous, melanoma occurs.

In Japan, the incidence of melanoma varies from 1.5 to 2 people in 100,000 in the general population. Thus, it is estimated that approximately 1,500 to 2,000 people develop melanoma per year. On the other hand, in the Western countries, more than a dozen of people develop melanoma in 100,000 in the general population. In particular, in Australia, twenty or more people develop such melanoma in 100,000 in the general population, and thus it is said that the incidence of melanoma in Australia is the highest in the world. Under such circumstances, people who live in Europe, the United States, and Australia are interested in melanoma, and they pay attention to the occurrence of melanoma. In addition, the frequency of occurrence of melanoma has been increasing, particularly among Caucasians, as a result of an increase in exposure to ultraviolet rays due to a reduction in the ozone layer in the atmosphere caused by environmental destruction. Moreover, the occurrence of melanoma tends to be increasing year after year in Japan as well. According to recent studies, the annual death toll from melanoma in Japan has increased to approximately 450. Melanoma develops regardless of age. However, the incidence of this disease increases for those over 40, and it is the highest for those in their 60's and 70's. The onset of this disease in childhood is extremely rare, but this does not mean that the disease never develops in childhood. Recently, the occurrence of melanoma tends to be increasing in young patients in their 20's and 30's. Melanoma develops regardless of sex, and both male and female patients suffer from this disease. In the case of Japanese patients, the site at which melanoma is most likely to develop is the sole (the sole of the foot), and it accounts for 30% of all cases of melanoma. As characteristics of Japanese patients, melanoma also develops in the foot and the nail portions of the fingers. In addition, as in the case of Western patients, melanoma develops in all parts of the skin, such as the body, hand, foot, face, and head, among Japanese patients as well.

First, the present inventors have performed genome-wide gene expression analysis, including regarding 23,040 kinds of human genes, utilizing cDNA microarray analysis. The inventors have analyzed expression profiles of these genes in 20 cases of primary hepatocellular carcinomas and in various types of normal organs including those present in the prenatal period. As a result, the inventors have found that glypican-3 (GPC3) is expressed in the liver, kidney, and lung during the prenatal period, and also that such glypican-3 is highly expressed in many hepatocellular carcinomas, although it is hardly ever expressed in normal adult organs, although it is expressed in placenta. The inventors have further reported that such GPC3 is a secretory protein, that such GPC3 can be detected in the serum of 40% of hepatocellular carcinoma patients by the ELISA method, and that this is useful as a novel tumor marker of hepatocellular carcinoma (Nakatsura, T. et al., Biochem. Biophys. Res. Commun. 306, 16-25 (2003)). Moreover, they have also reported that GPC3 is detected in the serum of melanoma patients, and that it is also useful as a tumor marker of melanoma (Nakatsura, T. et al., Clin. Cancer Res. 10: 6612-6621 (2004)).

The present inventors have already identified a GPC3 peptide, which binds to HLA-A24 and is presented to a human killer T cell, and which is useful for an immunotherapy that targets patients with HLA-A24 positive hepatocellular carcinoma or melanoma. The inventors have carried out an animal experiment using BALB/C mice that express mouse $K^d$ molecules, to which a peptide having the same structure as a peptide binding to HLA-A24 binds. Through this, they have demonstrated the effectiveness of immunotherapy using the aforementioned peptide and have already reported the results (International Application No. PCT/JP2004/016374; International Filing Date: Oct. 28, 2004). In normal organs, since GPC3 is expressed only in placenta and in the liver in the prenatal period, even when an immunotherapy targeting GPC3 is carried out to suppress tumor growth, adverse events such as autoimmune disease do not occur. This has been confirmed by an experiment using mice.

To date, with regard to glypican-3 (GPC3) as a tumor rejection antigen, the present inventors have identified a peptide, which is mainly presented by HLA-A24 to a killer T cell (International Application No. PCT/JP03/10459; International Filing Date: Aug. 19, 2003). However, with only such peptides presented by HLA-A24 to killer T cells, peptide vaccines can be administered to only the 60% of Japanese people who have HLA-A24. If a peptide presented to a killer T cell by HLA-A2, to which 40% of Japanese people test positive, can be identified, approximately 85% of Japanese people can become the targets of the two types of peptide vaccines. Furthermore, since Caucasians in the Western countries the frequency of HLA-A2 is relatively high, such a peptide presented by HLA-A2 can be applied to many Western people. Accordingly, it is an important object to identify the aforementioned peptide presented by HLA-A2 to a killer T cell. In particular, since melanoma is a cancer, which frequently develops in Caucasians in the Western countries and for which an immunotherapy is effective, and further, since hepatocellular carcinoma has also been rapidly increasing in the Western countries, it is assumed that there would be a large number of patients, for whom an immunotherapy using HLA-A2-binding GPC3 peptide can be applied.

DISCLOSURE OF THE INVENTION

Problems to be Solved by the Invention

It is an object of the present invention to identify peptides presented by HLA-A2 to a killer T cell, so as to provide a means for carrying out an immunotherapy, which is able to target approximately 40% of Japanese patients suffering from several types of cancers, which express GPC3 at a high level.

Means for Solving the Problems

Previously, the present inventors had identified glypican-3 (GPC3) as a novel carcinoembryonic protein that is specifically and excessively expressed in human hepatocellular carcinoma, based on cDNA microarray analysis. The inventors had further clarified that a soluble GPC3 protein is detected in the serum of a patient with hepatocellular carcinoma, and that such GPC3 can be a novel tumor marker of hepatocellular carcinoma. The present inventors had discovered that GPC3 is expressed in a mouse melanoma cell line B16 and is highly expressed at a high level in melanoma, as well as in hepatocellular carcinoma. Thus, the inventors had thought that GPC3 can also become a useful tumor marker of melanoma. As a result of a confirmatory experiment, they had found that GPC3 acts as a tumor marker of melanoma enabling an early diagnosis, which had never been realized so hr. This time, the present inventors have stimulated human CD8-positive killer T cells by coculturing them in vitro, together with human peripheral blood monocyte-derived dendritic cells, to which a human GPC3 peptide having an HLA-A2-binding motif had been pulsed, thereby inducing GPC3 peptide-specific killer T cells. The presence or absence of induction of killer T cells specific for each GPC3 peptide was detected by an ELISPOT method detecting γ-interferon (IFN-γ) generated by the activated killer T cells recognizing peptides presented by HLA-A2, and a novel GPC3 peptide that could be a candidate for a target antigen applicable to an immunotherapy was identified.

That is to say, the present invention provides the following features of invention.

(1) A peptide of any of the following (A) or (B):
(A) a peptide, which has the amino acid sequence as shown in any one of SEQ ID NOS: 1 to 3; or
(B) a peptide, which has an amino acid sequence comprising a substitution or addition of one or two amino acids with respect to the amino acid sequence as shown in any one of SEQ ID NOS: 1 to 3, and which has ability to induce killer T cells.
(2) An immune inducer used for cancers, which comprises at least one type of the peptide of (1) above.
(3) A pharmaceutical for treating and/or preventing tumors, which comprises at least one type of the peptide of (1) above.
(4) An agent for inducing antigen-presenting cells having high ability to induce tumor-reactive T cells, which comprises the peptide of (1) above.
(5) An agent for inducing antigen-presenting cells having high ability to induce tumor-reactive T cells, which comprises a gene encoding a peptide of any of the following (A) or (B):
(A) a peptide, which has the amino acid sequence as shown in any one of SEQ ID NOS: 1 to 3; or
(B) a peptide, which has an amino acid sequence comprising a substitution or addition of one or two amino acids with respect to the amino acid sequence as shown in any one of SEQ ID NOS: 1 to 3, and which has ability to induce killer T cells.
(6) An agent for inducing tumor-reactive T cells, which comprises the peptide of (1) above.
(7) An antibody against the peptide of (1) above.
(8) A helper T cell, a killer T cell, or an immunocyte population comprising such cells, which is induced using the peptide of (1) above.
(9) An antigen-presenting cell, which presents a complex consisting of an HLA molecule and the peptide of (1) above.
(10) The antigen-presenting cell of (9) above, which is induced using the agent of (4) or (5) above.

Best Mode for Carrying out the Invention (1) Peptide of the Present Invention, and Immune Inducer Comprising the Same Used for Cancers The peptide of the present invention is any peptide of the following (A) or (B):
(A) a peptide, which has the amino acid sequence as shown in any one of SEQ ID NOS: 1 to 3; or
(B) a peptide, which has an amino acid sequence comprising a substitution or addition of one or two amino acids with respect to the amino acid sequence as shown in any one of SEQ ID NOS: 1 to 3, and which has ability to induce killer T cells.

The term "peptide having ability to induce killer T cells" is used in the present specification to mean a peptide having a T cell-inducing activity of stimulating killer T cells (cytotoxic T lymphocytes/CTL).

A method for obtaining/producing the peptide of the present invention is not particularly limited. Either a chemically synthesized protein, or a recombinant protein produced by genetic recombination, may be used.

When a chemically synthesized peptide is obtained, the peptide of the present invention can be synthesized by a chemical synthesis method such as an Fmoc method (fluorenylmethyloxycarbonyl method) or a tBoc method (t-butyloxycarbonyl method), for example. In addition, the peptide of the present invention can also be synthesized using various types of commercially available peptide synthesizers.

When the peptide of the present invention is produced in the form of a recombinant protein, DNA having a nucleotide sequence encoding the aforementioned peptide, a mutant thereof, or a homologue thereof is obtained, and it is then introduced into a suitable expression system, so as to produce the peptide of the present invention.

As an expression vector, a vector capable of autonomously replicating in a host cell or capable of being incorporated into the chromosome of a host cell may preferably be used. An expression vector comprising a promoter at a position capable of expressing a gene encoding the peptide is used. In addition, a transformant having a gene encoding the peptide of the present invention can be produced by introducing the aforementioned expression vector into a host. As a host, any one of a bacterium, yeast, an animal cell, and an insect cell may be used. An expression vector may be introduced into a host according to a known method, depending on the type of such a host.

In the present invention, the transformant as produced above is cultured, and the peptide of the present invention is then generated and accumulated in a culture. Thereafter, the peptide of the present invention is collected from the culture, so as to isolate a recombinant peptide.

When such a transformant is a prokaryote such as *Escherichia coli* or a eukaryote such as yeast, a medium used for culturing such microorganisms may be either a natural medium or a synthetic medium, as long as it contains a carbon source, a nitrogen source, inorganic salts, and the like that can be assimilated by the aforementioned microorganisms, and it is able to efficiently carry out the culture of the transformant. Moreover, such culture may be carried out under conditions that are commonly applied for culturing the aforementioned microorganisms. After completion of the culture, the peptide of the present invention may be isolated and purified from the culture of the transformant according to a common method of isolating and purifying a peptide.

A peptide having an amino acid sequence comprising a substitution or addition of one or two amino acids with respect to the amino acid sequence as shown in any one of SEQ ID NOS: 1 to 3 can be appropriately produced or acquired by persons skilled in the art based on information regarding the nucleotide sequence of DNA encoding the amino acid sequence as shown in any one of SEQ ID NOS: 1 to 3. That is to say, a gene encoding a peptide which has an amino acid sequence comprising a substitution or addition of one or two amino acids with respect to the amino acid sequence as shown in any one of SEQ ID NOS: 1 to 3 and has ability to induce killer T cells, can be produced by any given method known to persons skilled in the art, such as chemical synthesis, genetic engineering means, or mutagenesis. For example, site-directed mutagenesis as a genetic engineering means is useful because it is a means for introducing a specific mutation into a specific position. Such site-directed mutagenesis can be carried out by a method described in Molecular Cloning: A laboratory Manual, $2^{nd}$ Ed., Cold Spring Harbor Laboratory, Cold Spring Harbor, N.Y., 1989 (hereinafter abbreviated as Molecular Cloning $2^{nd}$ Ed.), Current Protocols in Molecular Biology, Supplement 1 to 38, John Wiley & Sons (1987-1997) (hereinafter abbreviated as Current Protocols in Molecular Biology), etc.

As described later in examples, the aforementioned peptide of the present invention is able to induce immunity against cancers. Thus, the present invention provides an immune inducer used for cancers, which comprises the peptide of the present invention.

The immune inducer of the present invention used for cancers is used in vitro or in vivo, and preferably in vitro, so that it can induce a helper T cell, a killer T cell, or an immunocyte population comprising such cells, thereby imparting immunity against cancers.

(2) Antibody of the Present Invention

The present invention also relates to an antibody that recognizes a part or all of the aforementioned peptide of the present invention as an epitope (antigen), and a killer T cell induced by in vitro stimulation using the aforementioned protein or peptide. In general, such a killer T cell exhibits an antitumor activity that is stronger than that of an antibody.

The antibody of the present invention may be either a polyclonal antibody or a monoclonal antibody. Such an antibody can be produced by a common method.

For example, a polyclonal antibody can be produced by immunizing a mammal or apes with the peptide of the present invention used as antigen, then collecting blood from the mammal or apes, and then separating and purifying an antibody from the collected blood. For example, mammals or apes, such as a mouse, a hamster, a guinea pig, a chicken, a rat, a rabbit, a canine, a goat, a sheep, or a bovine, can be immunized. Such an immunization method is known to persons skilled in the art. For example, an antigen may be administered 2 or 3 times at intervals of 7 to 30 days. As a dosage, approximately 0.05 to 2 mg of antigen can be administered once, for example. An administration mute is not particularly limited, and subcutaneous administration, intracutaneous administration, intraperitoneal administration, intravenous administration, intramuscular administration, etc. can be selected, as appropriate. Moreover, an antigen can be dissolved in a suitable buffer, for example, a suitable buffer that contains a complete Freund's adjuvant or a commonly used adjuvant such as aluminum oxide, and it can be used.

The thus immunized mammal or apes is bred for a certain period of time. Thereafter, if the antibody titer increases, a booster can be carried out using 100 to 1,000 μg of antigen, for example. One or two months after the final immunization, blood is collected from the immunized mammal or apes. The thus collected blood is then separated and purified by an ordinary method including centrifugation, precipitation using ammonium sulfate or polyethylene glycol, chromatography such as gel filtration chromatography, ion exchange chromatography, or affinity chromatography, etc., so as to obtain a polyclonal antibody recognizing the peptide of the present invention in the form of a polyclonal antiserum.

On the other hand, a monoclonal antibody can be obtained by preparing a hybridoma. For example, such a hybridoma can be obtained by cell fusion of an antibody-generating cell and a myeloma cell. A hybridoma that generates the monoclonal antibody of the present invention can be obtained by the following cell fusion method.

As an antibody-generating cell, a splenic cell, a lymph node cell, a B lymphocyte, or the like obtained from the immunized animal is used. As an antigen, the peptide of the present invention is used. As an animal to be immunized, a mouse, a rat, or the like can be used. An antigen is administered to such an animal according to an ordinary method. For example, a suspension or emulsified liquid comprising an adjuvant such as a complete Freund's adjuvant or incomplete Freund's adjuvant and the peptide of the present invention used as an antigen is administered to an animal via intravenous administration, subcutaneous administration, intracutaneous administration, intraperitoneal administration, etc., several times, so as to immunize the animal. Thereafter, an antibody-generating cell such as a splenic cell is obtained from the immunized animal, and the thus obtained splenic cell is then fused with a myeloma cell according to a known method (G. Kohler et al., Nature, 256 495 (1975)), thereby producing a hybridoma.

Examples of a myeloma cell strain used in cell fusion include a P3X63Ag8 strain, a P3U1 strain and an Sp2/0 strain, in the case of a mouse. When such cell fusion is carried out, a fusion promoter such as polyethylene glycol or Sendai virus is used. For selection of a hybridoma after completion of the cell fusion, a hypoxanthine aminopterin thymidine (HAT) medium is used according to an ordinary method. The hybridoma obtained as a result of the cell fusion is cloned by a limiting dilution method. Further, as necessary, screening is carried out by an enzyme immunoassay using the peptide of the present invention, so as to obtain a cell strain that generates a monoclonal antibody specifically recognizing the peptide of the present invention.

In order to produce a monoclonal antibody of interest from the thus obtained hybridoma, the hybridoma may be cultured by a common cell culture method or ascites formation method, and the monoclonal antibody of interest may be then purified from the culture supernatant or ascites. The monoclonal antibody may be purified from the culture supernatant or ascites according to an ordinary method. For example, ammonium sulfate fractionation, gel filtration, ion exchange chromatography, affinity chromatography, and other methods may be combined as appropriate and used.

Moreover, the fragments of the aforementioned antibody are also included in the scope of the present invention. Examples of such an antibody fragment include an F(ab')2 fragment and an Fab' fragment.

(3) Helper T Cell, Killer T Cell, or an Immunocyte Population Comprising Such Cells The present invention also relates to a helper T cell, a killer T cell, or an immunocyte population comprising such cells, which is induced by in vitro stimulation using the peptide of the present invention. For example, when peripheral blood lymphocytes or tumor-infiltrating lymphocytes are stimulated in vitro using the peptide of the present invention, tumor-reactive activated T cells are induced. The thus activated T cells can be effectively used for an adoptive immunotherapy. Furthermore, dendritic cells that are strong antigen-presenting cells are allowed to express the peptide of the present invention in vivo or in vitro, and the antigen-expressing dendritic cells are then used to carry out immune induction.

Preferably, a helper T cell, a killer T cell, or an immunocyte population comprising such cells can be induced by in vitro stimulation using the peptide of the present invention and an immunostimulator. Examples of such an immunostimulator used herein include a cell growth factor and a cytokine.

The thus obtained helper T cell, killer T cell, or immunocyte population comprising such cells is transferred into a body, so that tumor can be suppressed and that cancer can be prevented and/or treated.

Furthermore, using the peptide of the present invention, a helper T cell, a killer T cell, or an immunocyte population comprising such cells, which is capable of suppressing tumor as described above, can be produced. Accordingly, the present invention provides a cell culture solution comprising the peptide of the present invention. Using such a cell culture solution, a helper T cell, a kilter T cell, or an immunocyte population comprising such cells, which is capable of suppressing tumor can be produced. Still further, the present invention also provides a cell culture kit for producing a helper T cell, a killer T cell, or an immunocyte population comprising such cells, which comprises the aforementioned cell culture solution and a cell culture vessel.

(4) Pharmaceutical of the Present Invention for Treating and/or Preventing Tumor (Cancer Vaccine)

Since the peptide of the present invention is able to induce cancer cell-specific killer T cells, it can be expected as an agent for treating and/or preventing cancer. For example, bacteria such as BCG (Bacillus Calmette-GuErin) transformed with recombinant DNA produced by incorporating a gene encoding the peptide of the present invention into a suitable vector, or viruses such as vaccinia virus, into the genome of which DNA encoding the peptide of the present invention has been incorporated, can be effectively used as a vaccine for treating and/or preventing human cancers. It is to be noted that the dosage and administration method of such a cancer vaccine are the same as those in the case of an ordinary smallpox vaccination or BCG vaccination.

That is to say, DNA encoding the peptide of the present invention (which is used as is, or is in the form of plasmid DNA incorporated into an expression vector), or a recombinant virus or recombinant bacteria comprising the aforementioned DNA, can be administered as a cancer vaccine to mammals including a human, directly or in a state where it is dispersed in an adjuvant. Likewise, the peptide of the present invention can also be administered as a cancer vaccine in a state where it is dispersed in an adjuvant.

Examples of an adjuvant used in the present invention include an incomplete Freund's adjuvant, BCG trehalose dimycolate (TDM), lipopolysaccharide (LPS), an alum adjuvant, and a silica adjuvant. From the viewpoint of ability to induce antibody, an incomplete Freund's adjuvant (IFA) is preferably used.

The type of a cancer is not particularly in the present specification. Specific examples of a cancer include esophageal cancer, breast cancer, thyroid cancer, colon cancer, pancreatic cancer, malignant melanoma (melanoma), malignant lymphoma, osteosarcoma, pheochromocytoma, head and neck cancer, uterine cancer, ovarian cancer, brain tumor, chronic myelogenous leukemia, acute myelogenous leukemia, kidney cancer, prostatic cancer, lung cancer, stomach cancer, hepatic cancer, gallbladder cancer, testicular cancer, thyroid cancer, bladder cancer, and sarcoma.

The peptide of the present invention acts as a T cell epitope and induces a cancer cell-specific killer T cell. Thus, the peptide of the present invention is useful as an agent for preventing and/or treating human cancers. In addition, if the antibody of the present invention is able to inhibit the activity of GPC3 as a cancer antigen, it is also useful as an agent for preventing and/or treating human cancers. As an actual usage, the peptide or antibody of the present invention can be administered as an injection product, directly or together with a pharmaceutically acceptable carrier and/or diluent, and as necessary, also together with the below-mentioned auxiliary substances. Moreover, the peptide or antibody of the present invention can also be administered by a method such as spraying, via transdermal absorption through mucosa. The term "carrier" is used herein to mean human serum albumin, for example. In addition, as a diluent, PBS, distilled water, or the like can be used.

As a dosage, the peptide or antibody of the present invention can be administered within the range between 0.01 and 100 mg per adult per administration. However, the dosage is not limited to the aforementioned range. The dosage form is not particularly limited, either. A freeze-dried product, or a granule produced by adding an excipient such as sugar, may also be available.

Examples of an auxiliary substance, which may be added to the agent of the present invention to enhance tumor-reactive T cell-inducing activity, include: muramyl-dipeptide (MDP); bacterial components such as BCG bacteria; ISCOM described in Nature, vol. 344, p. 873 (1990); saponin QS-21 described in J. Immunol. vol. 148, p. 1438 (1992); liposome; and aluminum oxide. Further, immunostimulators such as lenthinan, schizophyllan, or Picibanil may also be used as auxiliary substances. Other examples of products used herein as auxiliary substances include: cytokines for enhancing the growth or differentiation of T cells, such as IL-2, IL-4, IL-12, IL-1, IL-6, or TNF; α galactosylceramide for activating NKT cells; CpG that binds to a Toll-like receptor to activate a innate immune system; and lipopolysaccharide (LPS).

Furthermore, the aforementioned antigen peptide is added in vitro to cells collected from a patient, or (allogeneic) cells of anyone else who shares several HLA alleles, followed by antigen presentation of the cells. Thereafter, the cells are administered into the blood vessel of the patient, so that killer T cells can be effectively induced in the body of the patient. Further, the present peptide is added to the peripheral blood lymphocytes of a patient, and the obtained mixture is then cultured in vitro. Thereby, killer T cells can be induced in vitro, and they can be then returned to the blood vessel of the patient. Such a therapy involving cell transfer has already been carried out as a method for treating cancers, and thus it is a method well known to persons skilled in the art.

By introducing the peptide of the present invention into a body, killer T cells are induced and activated, and as a result, an antitumor effect can be anticipated. Moreover, when lymphocytes are stimulated by the peptide of the present invention in vitro, activated T cells are induced. The activated T cells are injected into an affected area. Thus, this technique can be effectively used for an adoptive immunotherapy.

The present invention will be further described in the following examples. However, these examples are not intended to limit the scope of the present invention.

EXAMPLES

Example 1

(1) Selection of GPC3 Peptide Exhibiting Binding Ability to HLA-A2

The amino acid sequence of human GPC3 was searched by a BIMAS system, and 4 types of sequences having an estimated binding affinity for HLA-A2 of 20 or greater were selected.

TABLE 1

| Peptide | position | Amino acid sequence of peptide | Binding affinity score |
|---------|----------|-------------------------------|------------------------|
| GPC3 | 44-52 | RLQPGLKWV (SEQ ID NO: 1) | 879 |
| GPC3 | 144-152 | FVGEFFTDV (SEQ ID NO: 2) | 828 |
| GPC3 | 155-163 | YILGSDINV (SEQ ID NO: 3) | 162 |
| GPC3 | 169-177 | ELFDSLFPV (SEQ ID NO: 4) | 1055 |

Example 2

Induction of Human Killer T Cells by HLA-A2-Binding GPC3 Peptide (1) Blood Collection Informed consent was obtained from HLA-A2-positive hepatocellular carcinoma patients, who were in therapy at Gastroenterological Surgery, Kumamoto University School of Medicine, and at Hospital East, the National Cancer Center. Thereafter, 30 ml of blood sample was obtained from individual patients, and peripheral blood mononuclear cells were then isolated using Ficoll-Conray density-gradient centrifugation method according to the previously reported method (Nakatsura, T et al., Eur. J. Immunol. 32, 826-836 (2002)).

(2) Separation of CD8-positive Cells and CD14-positive Cells from Peripheral Blood Mononuclear Cells and Induction of Killer T Cells From the isolated peripheral blood mononuclear cells, killer T cells were induced by the previously reported method (Monji, M et al., Clin Cancer Res 10, 6047-6057, 2004). First, CD8-positive cells and CD14-positive cells were separated from the peripheral blood mononuclear cells using MACS. The CD14-positive cells were cultured in the presence of GM-CSF (100 ng/ml) and IL-4 (20 ng/ml) for 5 days, so that differentiation of dendritic cells was induced. Thereafter, TNF-α (20 ng/ml) was added thereto for maturation. On the $7^{th}$ day, each GPC3 peptide (10 μM) was added thereto, and co-culture with CD8-positive cells was then carried out. This antigen stimulation with autologous CD14-positive cell-derived dendritic cells was repeated 3 or 4 times every week, so that peptide-specific killer T cells were induced. During the induction, half a medium was exchanged with a fresh one every two days, and IL-2 was added thereto in a concentration of 10 U/ml.

(3) Analysis of Activity of GPC3-specific Killer T Cells by ELISPOT Method

The presence or absence of a killer T cell that reliably and specifically reacts with GPC3 and produces IFN-γ in the thus induced killer T cells was examined by the ELISPOT method. IFN-γ was detected using ELISPOT Human IFN-γ ELISPOT set (BD). When a killer T cell (effector) reacts with a stimulator cell (target) to generate IFN-γ, each IFN-γ is detected as a red spot. As target cells, SK-Hep-1 cells as parent cells, which are HLA-A2 positive and do not express GPC3, and SK-Hep-1/GPC3 cells, in which GPC3 gene has been introduced into SK-Hep-1 cells to express GPC3 protein, were used. First, an ELISPOT plate (BD Bioscience) was coated with an anti-human IFN-γ antibody for 18 hours. Thereafter, it was blocked with 10% FCS/RPMI for 2 hours. The effector cells (100 μl/well) were mixed with the target cells (100 μl/well), and the mixture was then cultured at 37° C. for 22 hours. An experiment was carried out at a ratio between effectors and targets (E/T ratio) of 5:1. Thereafter, the plate was washed with sterilized water, and it was then allowed to react with a biotinylated anti-human IFN-γ antibody for 2 hours, and then with streptavidin-HRP for 1 hour. Thereafter, IFN-γ positive spots were detected with a substrate solution. The number of such spots was counted using automatic analysis software of MINERVA TECH. As a result, GPC3-specific killer T cell activity could be detected in the case of killer T cells induced by GPC3 44-52, 114-152, and 155-163 peptides. However, GPC3-specific killer T cell activity was not detected in the case of killer T cells induced by a GPC3 169-177 peptide (FIGS. 1 and 2). The analytical results of killer T cells induced by a representative GPC3 155-163 peptide are shown in FIG. 1.

(4) Analysis of Cytotoxic Activity of Killer T Cells by Cytotoxicity Test

The cytotoxic activity of the induced killer T cells was analyzed by a cytotoxicity test using, as stimulated cells, SK-Hep-1 cells as parent cells, which are HLA-A2-positive and do not express GPC3, and SK-Hep-1/GPC3 cells, in which GPC3 gene has been introduced into SK-Hep-1 cells to express GPC3 protein. The cytotoxic activity of killer T cells was evaluated by a cytotoxic test using Terascan VP. First, target cells were fluorescently labeled with a calcein AM staining solution at 37° C. for 30 minutes. Such cells were co-cultured with killer T cells on a Coster 96-well half area plate, and fluorescently labeled cells were then detected over time, thereby measuring the degree of cytotoxicity. The analysis was carried out using cytotoxicity test computing software CalCT-961 of MINERVA TECH, which was used in a fluorescence method. An experiment was carried out at an E/T ratio of 20:1. As a result, a GPC3-specific cytotoxic activity was confirmed in killer T cells induced by GPC3 44-52, 144-152, and 155-163 peptides. However, GPC3-specific cytotoxic activity was not observed in killer T cells induced by a GPC3 169-177 peptide (FIG. 2).

INDUSTRIAL APPLICABILITY

The effectiveness of a cancer immunotherapy that targets a GPC3 peptide presented by HLA-A24 was confirmed by an animal experiment using mice. However, using such peptides presented by HLA-A24 to killer T cells, peptide vaccines could be administered to only the 60% of Japanese people. This time, by identifying a peptide presented to a killer T cell by HLA-A2, approximately 85% of Japanese people can become the targets of the combination of two types of peptide vaccines. If the effectiveness of experimental therapeutics using a peptide presented by HLA-A2 to a killer T cell is demonstrated, it is highly likely that such a peptide will be clinically applied also to Caucasians in the Western countries. In addition, by identifying such a peptide presented by HLA-A2 to a killer T cell, the identified peptide cannot only be applied to 40% of Japanese patients suffering from hepatocellular carcinoma and melanoma, but it can also be applied to many Caucasians in which the frequency of HLA-A2 is higher that that in the Japanese.

BRIEF DESCRIPTION OF THE DRAWINGS

FIG. 2 shows the results of ELISPOT analysis and a cytotoxicity test. CD8 positive T cells were selected from the peripheral blood of an HLA-A2-positive hepatocellular carcinoma patient, and the selected cells were then stimulated by dendritic cells derived from monocytes loaded with each GPC3 peptide. Whether or not the thus obtained killer T cells specifically reacted with GPC3 expression cells and produced IFN-γ was examined by an ELISPOT assay. Moreover, whether or not the aforementioned killer T cells specifically killed the GPC3-expressing cells was examined by a cytotoxicity test. As target cells, SK-Hep-1 cells as parent cells, which were HLA-A2 positive and did not express GPC3, and SK-Hep-1/GPC3 cells, in which GPC3 gene has been introduced into SK-Hep-1 cells to express GPC3 protein, were used. As a result, killer T cells induced by GPC3 44-52 (SEQ ID NO: 1), 144-152 (SEQ ID NO: 2), and 155-163 (SEQ ID NO: 3) peptides GPC3-specifically recognized SK-Hep-1/GPC3 cells and produced IFN-γ, and they also exhibited strong cytotoxic activity. In contrast, killer T cells induced by a GPC3 169-177 (SEQ ID NO: 4) peptide did not exhibit GPC3-specific killer T cell activity. From such results, it was demonstrated that the GPC3 44-52, 144-152, and 155-163 peptides are epitope peptides capable of inducing GPC3-specific killer T cells.

Figure 1:
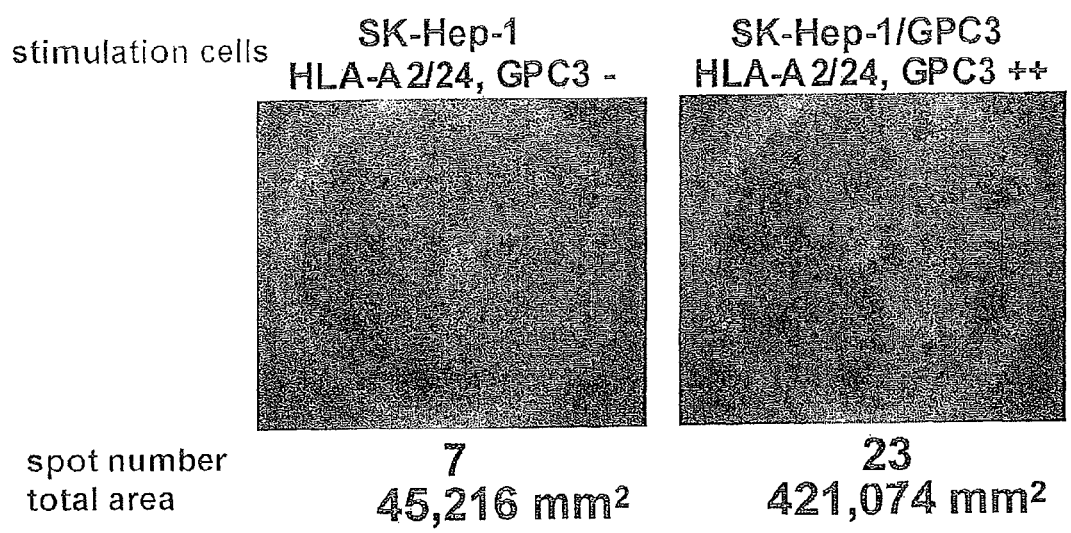
FIG. 1 shows representative results obtained by ELISPOT analysis, IFN-γ produced by killer T cells, which have specifically recognized GPC3 peptides and have been activated. With regard to killer T cells induced by stimulating CD8 positive cells in the peripheral blood of a hepatocellular carcinoma patient by dendritic cells derived from CD14 positive monocytes loaded with a GPC3 155-163 peptide, the number of spots and the total area of such spots in a case where SK-Hep-1/GPC3 cells, in which GPC3 gene has been introduced into SK-Hep-1 cells to express GPC3 protein, were used as stimulator cells (in the right-hand side of the figure), were significantly greater than those in a case where SK-Hep-1 cells as parent cells, which was HLA-A2-positive and did not express GPC3, were used as stimulator cells (in the left-hand side of the figure). From such results, it was determined that the GPC3 155-163 peptide is an epitope peptide capable of inducing GPC3-specific killer T cells.

What is claimed is:

1. An isolated antigen-presenting cell, which presents a complex consisting of an HLA molecule and a peptide consisting of the amino acid sequence as shown in any one of SEQ ID NOS: 1 to 3.

2. The isolated antigen-presenting cell of claim 1, which has been induced with a peptide consisting of the amino acid sequence as shown in any one of SEQ ID NOS: 1 to 3.

3. The isolated antigen-presenting cell of claim 1, which has been induced with a nucleic acid encoding a peptide which consists of the amino acid sequence as shown in any one of SEQ ID NOS: 1 to 3.

* * * * *